United States Patent [19]

Brown, deceased et al.

[11] 4,013,774

[45] Mar. 22, 1977

[54] INSECTICIDAL N-THIO-SUBSTITUTED CARBAMATES OF DIHYDROBENZOFURANOLS

[75] Inventors: Melancthon S. Brown, deceased, late of Berkeley, Calif., by Gustave K. Kohn, special administrator; Gustave K. Kohn, Berkeley, Calif.

[73] Assignee: Chevron Research Company, San Francisco, Calif.

[22] Filed: June 13, 1975

[21] Appl. No.: 587,195

Related U.S. Application Data

[60] Division of Ser. No. 490,178, July 29, 1974, Pat. No. 3,897,463, which is a division of Ser. No. 317,317, Dec. 21, 1972, Pat. No. 3,847,951, which is a continuation-in-part of Ser. Nos. 235,796, March 17, 1972, abandoned, and Ser. No. 235,797, March 17, 1972, abandoned, which is a continuation-in-part of Ser. No. 230,117, Feb. 28, 1972, Pat. No. 3,792,169, which is a division of Ser. No. 855,421, Sept. 4, 1969, Pat. No. 3,663,594, which is a continuation-in-part of Ser. No. 764,299, Oct. 1, 1968, abandoned, and Ser. No. 250,908, May 8, 1972, Pat. No. 3,843,689.

[52] U.S. Cl. .............................................. 424/285
[51] Int. Cl.² ........................................ A01N 9/28
[58] Field of Search .............. 424/285; 260/346.2 R

[56] References Cited

UNITED STATES PATENTS

| | | | |
|---|---|---|---|
| 3,474,171 | 10/1969 | Scharpf | 424/285 |
| 3,822,295 | 7/1974 | Serban et al. | 260/346.2 R |
| 3,847,951 | 11/1974 | Kohn et al. | 260/346.2 R |
| 3,897,463 | 7/1975 | Kohn et al. | 260/346.2 R |

*Primary Examiner*—Leonard Schenkman
*Attorney, Agent, or Firm*—J. A. Buchanan, Jr.; Dix A. Newell; Raymond Owyang

[57] ABSTRACT

This invention is directed to 2,3-dihydro-2,2-dialkyl benzofuranyl N-thio-substituted carbamates and their use as insecticides.

30 Claims, No Drawings

INSECTICIDAL N-THIO-SUBSTITUTED CARBAMATES OF DIHYDROBENZOFURANOLS

CROSS REFERENCE TO RELATED APPLICATIONS

This application is a division of application Ser. No. 490,178, filed July 29, 1974, now U.S. Pat. No. 3,897,463, which, in turn, is a division of application Ser. No. 317,317, filed Dec. 21, 1972, now U.S. Pat. No. 3,847,951, which, in turn, is a continuation-in-part of applications Ser. Nos. 235,796 and 235,797, filed Mar. 17, 1972, now abandoned, which are continuation-in-parts of application Ser. No. 230,117, filed Feb. 28, 1972, now U.S. Pat. No. 3,792,169 which in turn is a division of application Ser. No. 855,421, filed Sept. 4, 1969, now U.S. Pat. No. 3,663,594, which in turn is a continuation-in-part of application Ser. No. 764,299, filed Oct. 1, 1968, now abandoned; and U.S. Ser. No. 250,908, filed May 8, 1972, now U.S. Pat. No. 3,843,689.

BACKGROUND OF THE INVENTION

U.S. Pat. No. 3,474,171, issued to W. G. Scharpf on October 21, 1969, discloses that N-methyl-2,3-dihydro-2,2-dimethylbenzofuranyl carbamate is pesticidal. The carbamate of U.S. Pat. No. 3,474,171 is particularly effective as an insecticide and exhibits both high contact and systemic activity against a variety of insects.

Although the carbamate of U.S. Pat. No. 3,474,171 is a highly effective insecticide, it is toxic to mammals at fairly low dosages. For instance, the oral toxicity, $LD_{50}$ (rats), of N-methyl-2,3-dihydro-2,2-dimethylbenzofuranyl carbamate as established by test on laboratory animals is about 5-11 mg/kg. This high toxicity precludes the use of the carbamate of U.S. Pat. No. 3,474,171 in certain environments. Some countries completely prohibit the use of any insecticide having the high toxicity exhibited by the carbamate of U.S. Pat. No. 3,474,171.

SUMMARY OF THE INVENTION

It has now been found that N-thio-substituted 2,3-dihydro-2,2-dialkylbenzofuranyl carbamates combine a high degree of insecticidal activity with relatively low mammalian toxicity. This finding is especially surprising since structural modifications which decrease mammalian toxicity normally also decrease insecticidal activity proportionately. This unique combination of high insecticidal activity and low mammalian toxicity permit the use of the novel N-thio-substituted carbamates of this invention in environments in which the corresponding carbamates could not be used.

DESCRIPTION OF THE INVENTION

Compounds of Invention

The novel carbamate compounds of the invention are represented by the formula (I):

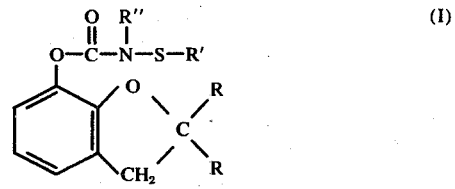

wherein:

R and R'' individually are hydrogen or alkyl of 1 to 4 carbon atoms, preferably methyl, and R' is alkyl of 1 to 12 carbon atoms, alkenyl of 2 to 12 carbon atoms, monocyclic or bicyclic aryl of 6 to 10 carbon atoms, alkyl of 2 to 12 carbon atoms substituted with 1 to 5 fluorine, chlorine or bromine atoms, alkenyl of 2 to 12 carbon atoms substituted with 1 to 5 fluorine, chlorine or bromine atoms, or monocyclic or bicyclic aryl of 6 to 10 carbon atoms substituted with 1 to 5 fluorine, chlorine or bromine atoms, or 1 to 2 nitro groups.

Illustrative aliphatic R' groups are alkyl groups, including cycloalkyl, such as methyl, ethyl, n-propyl, isopropyl, n-butyl, t-butyl, amyl, cyclopentyl, cyclohexyl, heptyl, 3-ethylamyl, 2-methylhexyl, n-hexyl, n-octyl, 4-methylheptyl, n-nonyl, n-decyl, 5-ethyloctyl, n-undecyl, n-dodecyl; alkenyl groups such as vinyl, propenyl, 3-butenyl, 2-butenyl, 5-hexenyl, 5-heptenyl, 3-heptenyl, 7-octenyl, 5-nonenyl, 7-nonenyl, 9-decenyl, 6-decenyl, 11-dodecenyl, 8-undecenyl; haloalkyl groups such as 2-fluoroethyl, 2-chloroethyl, 2,2-difluoroethyl, 1,2-dichloroethyl, 1,1,2,2-tetrachloroethyl, 1,2,2,2-tetrachloroethyl, 1,1,2,2-tetrabromoethyl, 1-chloro-2,2,2-tribromoethyl, pentchloroethyl, 3-chloropropyl, 4-bromobutyl, 3,5-dibromopentyl, 2,4,6-trichlorohexyl, 7-chloroheptyl, 11-bromododecyl, etc.; and haloalkenyl such as 1-chlorovinyl, 2-chlorovinyl, 2,2-dichlorovinyl, trichlorovinyl, tribromovinyl, 1-chloro-2,2-dibromovinyl, 3-fluoro-2-propenyl, 3-chloro-4-pentenyl, 6-chloro-9-decenyl, etc.

Illustrative aryl R' groups are aryl hydrocarbon groups such as phenyl; naphthyl, alkaryl groups of 7 10 carbon atoms, e.g., tolyl, xylyl, 4-ethylphenyl, 4-isopropylphenyl; aralkyl groups of 7 to 10 carbon atoms, e.g., benzyl, 3-phenylpropyl, 2-phenylethyl; halo- and nitro-substituted phenyl, alkaryl or aralkyl groups such as 4-chlorophenyl, 4-bromophenyl, 2,4-dichlorophenyl, 3,4-dichlorophenyl, 2-fluorophenyl, 2-chloro-4-methylphenyl, 3,5-dichlorophenyl, 2-bromophenyl, 4-fluorophenyl, 2,5-dibromophenyl, 2-bromo-4-chlorophenyl, p-chlorobenzyl, 2-(p-fluorophenyl)ethyl, 2-nitrophenyl, 3-nitrophenyl, 4-nitrophenyl, 2-chloro-5-nitrophenyl, 2-nitro-4-methylphenyl and 3,5-dinitrophenyl.

Preferred aliphatic R' groups are alkyl of 2 to 6 carbon atoms and haloalkyl of 2 to 3 carbon atoms. The halogen substituents of the haloalkyl R' group are preferably chlorine.

Preferred aryl R' groups are halo-substituted phenyls, especially those having 1 to 2 fluorine, chlorine or bromine substituents.

Representative compounds of formula (I) are N-methyl-N-methylthio-2,3-dihydro-7-benzofuranyl carbamate, N-methyl-N-methylthio-2,3-dihydro-2-methyl-7-benzofuranyl carbamate, N-methyl-N-methylthio-2,3-dihydro-2,2-dimethyl-7-benzofuranyl carbamate, N-methyl-N-ethylthio-2,3-dihydro-2,2-dimethyl-7-benzofuranyl carbamate, N-methyl-N-propylthio-2,3-dihydro-2,2-dimethyl-7-benzofuranyl carbamate, N-isobutylthio-2,3-dihydro-2,2-dimethyl-7-benzofuranyl carbamate, N-ethyl-N-butylthio-2,3-dihydro-2,2-diethyl-7-benzofuranyl carbamate, N-methyl-N-hexylthio-2,3-dihydro-2,2-dimethyl-7-benzofuranyl carbamate, N-methyl-N-decylthio-2,3-dihydro-2,2-dimethyl-7-benzofuranyl carbamate, N-methyl--dodecylthio-2,3-dihydro-2,2-dimethyl-7-benzofuranyl carbamate, N-butyl-N-vinylthio-2,3-dihydro-2-methyl-2-ethyl-7-benzofuranyl carbamate, N-butyl-N-propenylthio-2,3-dihydro-2,2-dipropyl-7-benzofuranyl carbamate, N-propyl-N-2-butenylthio-2,3-dihydro-2,2-dibutyl-7-benzofuranyl carbamate, N-methyl-N-3-heptenylthio-2,3-dihydro-2,2-dimethyl-7-benzofuranyl carbamate, N-2-bromoethylthio-2,3-dihydro-2,2-dimethyl-7-benzofuranyl carbamate, N-methyl-N-2,2-dichloroethylthio-2,3-dihydro-7-benzofuranyl carbamate, N-methyl-N-2,2,2-trifluoroethylthio-2,3-dihydro-2,2-dimethyl-7-benzofuranyl carbamate, N-methyl-N-2,2,2-trichloroethylthio-2,3-dihydro-2,2-dimethyl-7-benzofuranyl carbamate, N-methyl-N-1,2,2-tribromoethylthio-2,3-dihydro-2,2-dimethyl-7-benzofuranyl carbamate, N-methyl-N-1,2-difluoroethylthio-2,3-dihydro-2,2-dimethyl-7-benzofuranyl carbamate, N-methyl-N-2-bromoethylthio-2,3-dihydro-2,2-dimethyl-7-benzofuranyl carbamate, N-methyl-N-1,2,2,2-tetrachloroethylthio-2,3-dihydro-2,2-dimethyl-7-benzofuranyl carbamate, N-methyl-N-1,1,2,2-tetrachloroethylthio-2,3-dihydro-2,2-dimethyl-7-benzofuranyl carbamate, N-methyl-N-3,6-dibromohexylthio-2,3-dihydro-2,2-dimethyl-7-benzofuranyl carbamate, N-methyl-N-trichlorovinylthio-2,3-dihydro-2,2-dimethyl-7-benzofuranyl carbamate, N-tribromovinylthio-2,3-dihydro-2,2-dimethyl-7-benzofuranyl carbamate.

Representative compounds of formula (I) are N-α-naphthylthio-2,3-dihydro-2,2-dimethyl-7-benzofuranyl carbamate, N-methyl-N-phenylthio-2,3-dihydro-7-benzofuranyl carbamate, N-methyl-N-phenylthio-2,3-dihydro-2-methyl-7-benzofuranyl carbamate, N-methyl-N-phenylthio-2,3-dihydro-2,2-dimethyl-7-benzofuranyl carbamate, N-methyl-N-4-chlorophenylthio-2,3-dihydro-2,2-dimethyl-7-benzofuranyl carbamate, N-methyl-N-4-fluorophenylthio-2,3-dihydro-2,2-dimethyl-7-benzofuranyl carbamate, N-methyl-N-3,5-dichlorophenylthio-2,3-dihydro-2,2-dimethyl-7-benzofuranyl carbamate, N-methyl-N-2,4-dichlorophenylthio-2,3-dihydro-2,2-dimethyl-7-benzofuranyl carbamate, N-methyl-N-3-chloro-5-methylphenylthio-2,3-dihydro-2-methyl-7-benzofuranyl carbamate, N-ethyl-N-2-bromophenylthio-2,3-dihydro-2,2-dimethyl-7-benzofuranyl carbamate, N-methyl-N-4-methylphenylthio-2,3-dihydro-7-benzofuranyl carbamate, N-4-chlorophenylthio-2,3-dihydro-2-methyl-7-benzofuranyl carbamate, N-methyl-N-4-ethylthiophenylthio-2,3-dihydro-2,2-dimethyl-7-benzofuranyl carbamate, N-methyl-N-o-nitrophenylthio-2,3-dihydro-2,2-7-benzofuranyl carbamate, N-methyl-N-o-nitrophenylthio-2,3-dihydro-2,2-dimethyl-7-benzofuranyl carbamate, N-methyl-p-nitrophenylthio-2,3-dihydro-2,2-dimethyl-7-benzofuranyl carbamate.

Preferred compounds of formula (I) are those having mammalian acute oral toxicity, $LD_{50}$ (rats), of greater than 25 mg/kg, preferably greater than 50 mg/kg.

PREPARATION OF THE COMPOUNDS OF THE INVENTION

The compounds of the invention may be prepared by reacting a 2,3-dihydro-7-benzofuranyl carbamate with a sulfenyl halide as depicted in the following equation (1):

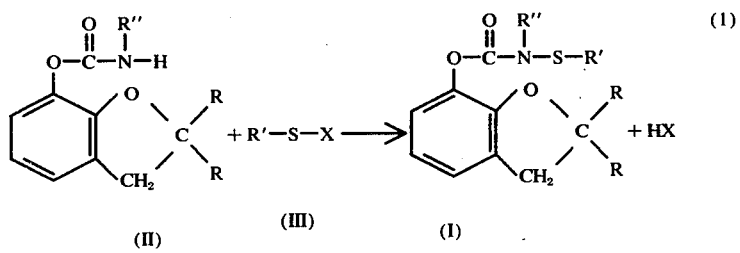

wherein R, R' and R" are of the same significance as defined in formula (I) and X is halogen.

The benzofuranyl carbamate starting material may be obtained by the method described in U.S. Pat. No. 3,356,690, issued to E. F. Orwoll on Dec. 5, 1967.

The reaction is preferably carried out in an aprotic organic solvent such as dimethylformamide, hexamethyltriamidophosphate, etc., wherein the quantity of solvent varies from 2 to 10 times the volume of the reactants. The sulfenyl halide compound is employed in amounts ranging from about 1 to 2 moles per mole of benzofuranyl carbamate. A soluble base is used in amounts ranging from about 1 to 2 moles per mole of the sulfenyl halide, to scavenge the hydrogen halide by-product. The preferred bases are the organic amines, such as triethylamine, pyridine, quinnucledine, etc.

The reaction is carried out by slowly adding the sulfenyl halide compound (III) to the benzofuranyl carbamate (II) and amine base dissolved in the solvent. The reaction temperature is maintained in the range of 15°–35° C, preferably 20°–30° C. The reactants are mixed and allowed to react at this temperature for ½–5 hours or until essentially no more amine hydrochloride is formed. The reaction is preferably carried out at atmospheric pressure.

The reaction product is isolated by adding a water insoluble organic solvent such as benzene, toluene, chloroform, or ether to the reaction mixture followed by sufficient water to form two layers. After separation, the aqueous layer is extracted with the organic solvent. The combined organic layer and extract is dried and the solvent removed by stripping at low temperature or by distillation to give the crude product which may be used as such or it may be purified by chromatography, crystallization, or the like.

An alternative method for preparing the compounds of formula (I) is by the reaction of the sodium salt of a 2,3-dihydro-7-hydroxybenzofuran with an appropriate N-thio-substituted carbbamoyl chloride, thus:

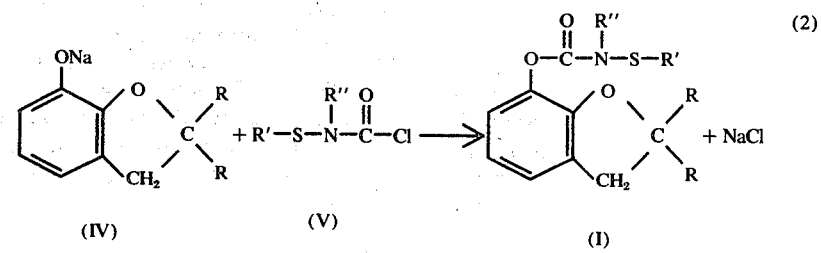

wherein R, R' and R'' are as defined previously. This reaction is the preferred method for preparing compounds of formula (I) wherein R' is haloalkyl.

The reaction (2) is carried out in an inert organic solvent such as benzene, toluene, chlorobenzene, or carbon tetrachloride. The sodium salt (IV) is prepared in situ from the corresponding benzofuranol by reaction with sodium metal, sodium hydride, butyl sodium, and the like. Then an equal molar amount of the carbamoyl chloride is added. The reaction is maintained at 20°–30° C. throughout the run. Workup of the product involves removal of the insoluble sodium chloride precipitate followed by evaporation of the solvent. The crude product obtained in this way may be used as such, or it may be purified by chromatography or crystallization.

The N-thio-substituted carbamoyl chloride (V) is prepared by the reaction of a sulfenylated amine and phosgene as depicted in the following equation (3):

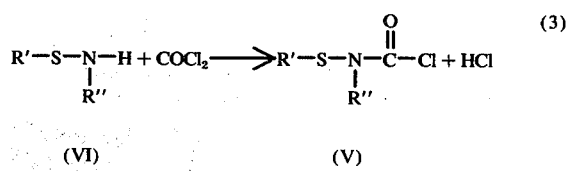

The reaction (3) is conducted by contacting the sulfenylated amine (VI) with phosgene in the presence of an acid acceptor and an inert reaction solvent or diluent. Illustrative organic solvents are aromatic compounds such as benzene, toluene, chlorobenzene; alkanes such as heptane and isooctane; cycloalkanes such as cyclohexane; and haloalkanes such as methylene dichloride. Other suitable organic solvents include nitriles such as acetonitrile and propionitrile; and dialkylamides such as dimethylformamide amide. The amount of organic solvent employed is generally from about 1 to 10 moles per mole of the sulfenylated amine reactant. Suitable acid acceptors include organic amines free of amino hydrogens, i.e., —N'H groups, such as organic tertiary amines and pyridine compounds. Illustrative organic tertiary amines include trialkylamines such as triethylamine, tripropylamine, N-methylpiperidine, etc. and illustrative pyridine compounds include pyridine, 2-methylpyridine, 3-methylpyridine, etc.

The molar ratio of the sulfenylated amine reactant (VI) and phosgene is generally about 2:1 to about 1:5, although molar ratios of about 1:1 to 1:2 are preferred. Suitable reaction temperatures vary from about 0° to 60° C, but preferably from 15° to 35° C. The reaction is conducted at or about atmospheric pressure. Typical pressures vary from about 1 to 10 atmospheres. The carbamoyl chloride product (V) is separated and recovered from the reaction mixture by conventional methods such as selective extraction, filtration, chromatography and the like.

The sulfenylated amine reactant (VI) employed in reaction (3) is prepared reacting an amine and a sulfenyl halide by known procedures. See, for example, U.S. Pat. No. 2,520,400, issued on Aug. 29, 1950, to C. M. Himel et al.

The compounds of formula (I) may also be prepared by reacting the chloroformate of an 2,3-dihydro-7-hydroxybenzofuran with an appropriate sulfenylated amine as depicted in the following equation (4):

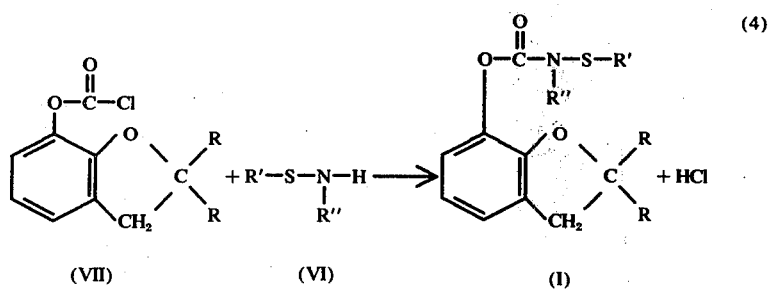

wherein R, R' and R'' have the same significance as previously defined.

The chloroformate (VII) is prepared from an appropriate 2,3-dehydro-7-hydroxybenzofuran by conventional methods. For example, the chloroformate VII may be prepared by the reaction of the 2,3-dihydro-7-hydroxybenzofuran and phosgene.

The reaction between the chloroformate (VII) and the sulfenylated amine (VI) is conducted by essentially the same procedures described for reaction (3).

The compounds of formula (I) wherein R' is alkenyl or haloalkenyl may also be prepared by dehydrohalogenation of the corresponding compound wherein R' is haloalkyl by conventional procedures. For example, a N-alkyl-N-trihalovinylthio-2,3-dihydro-2,2-dimethylbenzofuranyl carbamate may be prepared by treating a N-alkyl-N-tetrahaloethylthio-2,3-dihydro-2,2-dimethylbenzofuranyl carbamate with a strong base, e.g., sodium hydride, in liquid phase solution at a temperature of 0°-60° C.

The following examples illustrate methods which may be used to prepare the compounds of the invention. The compounds prepared by these methods are tabulated in Table I.

EXAMPLE 1

Preparation of
N-trichloromethylthio-N-methylthio-2,3-dihydro-2,2-dimethyl-7-benzofuranyl carbamate A solution of 37.2 g (0.2 mole) trichloromethylsulfenyl chloride in 100 ml of benzene was added dropwise to a solution of 6.2 g (0.2 mole) of methylamine and 20.2 g (0.2 mole) of triethylamine in 100 ml of benzene at a temperature of 5°-8° C. After the addition was completed, the reaction mixture was stirred for 10 minutes and then filtered to remove the triethylamine hydrochloride salt produced.

Into the resulting N-trichloromethylthio-N-methylamine filtrate solution was bubbled 19.8 g (0.2 mole) of phosgene at a temperature of 4°-8° C. The reaction mixture was stirred for 20 minutes, stored at about 0° C for 16 hours, and filtered. The filtrate was evaporated under reduced pressure to give 39.9 g of the N-trichloromethylthio-N-methylcarbamoyl chloride product.

Elemental analysis for $C_3Cl_4NOS$ showed:

|  | Calc. | Found |
|---|---|---|
| S % | 13.15 | 14.15 |
| Cl % | 58.6 | 54.45 |

A 7.16 sample of sodium hydride oil dispersion (50% NaH, 0.149 mole NaH) was added in small portions to a solution of 24.5 g (0.149 mole) of 2,3-dihydro-2,2-dimethyl-7-benzofuranol in 150 ml benzene. After the addition was completed, the reaction mixture was warmed to 45° C and stirred until hydrogen evolution ceased. The reaction mixture was cooled and 39.9 g of N-trichloromethylthio N-methylcarbamoyl chloride (prepared in Example 1) in 40 ml of benzene was added dropwise at about 25° C. After the carbamoyl chloride was added, the reaction mixture was stirred at about 25° C for 3 to 4 hours and stored at about 25° C for about 16 hours. The reaction mixture was then washed with water. The water washes were extracted with benzene. The combined organic solutions were dried over magnesium sulfate and evaporated under reduced pressure to give the crude product. The crude product was purified by chromatography (benzene eluant) and crystallization from hexane to give 21.5 g of N-methyl-N-trichloromethylthio-2,3-dihydro-2,2-dimethyl-7-benzofuranyl carbamate, m.p., 88.5°-89.5° C. The elemental analysis on the product is tabulated in Table I.

EXAMPLE 2

Preparation of
2,3-dihydro-2,2-dimethyl-7-benzofuranyl N-methyl N-1,1,2,2-tetrachloroethylthiocarbamate A solution of 3.1 g (0.1 mole) methylamine and 10.1 g (0.1 mole) triethylamine in 100 ml acetonitrile was added dropwise to a solution of 23.4 g (0.1 mole) 1,1,2,2-tetrachloroethylsulfenyl chloride in 200 ml acetonitrile at about 0°-5° C. Into the reaction mixture was then bubbled 9.9 g (0.1 mole) phosgene. The reaction was stirred at about 25° C for about 17 hours. The acetonitrile solvent was evaporated under reduced pressure and the residue was diluted with benzene and filtered to give a filtrate solution of N-1,1,2,2-tetrachloroethylthio N-methyl carbamoyl chloride in benzene.

A 500 ml Erlenmeyer flask was charged with 8.0 g (0.049 mole) of 2,3-dihydro-2,2-dimethyl-7-hydroxybenzofuran dissolved in 100 ml of benzene. To this, there was added in small increments, 2.35 g (0.049 mole) of a 50% sodium hydride composition. The resulting solution was added to 14.6 g (0.050 mole) of N-1,1,2,2-tetrachloroethylthio N-methyl carbamoyl chloride (prepared above) dissolved in 50 ml of benzene. After stirring this mixture for one-half hour, the insoluble precipitate was removed by filtration. The solvent was then removed by evaporation. The resulting oil was chromatographed on silica gel using benzene/hexane eluant to give 9.8 g of the product, m.p. 84°-84.5° C. The infrared spectra showed strong adsorption peaks at 5.8, 7.75, 8.0, 8.2, 8.7, 8.8, 9.05, 11.45, 13.1 and 14.2 microns. An NMR spectrum showed adsorption peaks at 1.53 ppm (S), 6H; 3.1 ppm (S), 2H; 3.6 ppm (S) 3H; 6.65 ppm (S), 1H; and 6.7-7.3 ppm (M), 3H. The elemental analysis on the product is tabulated in Table I.

EXAMPLE 3

Preparation of
2,3-dihydro-2,2-dimethyl-7-benzofuranyl N-methyl N-methylthiocarbamate In a flask, 15.00 g (0.068 mole) of 2,3-dihydro-2,2-dimethyl-7-benzofuranyl N-methyl carbamate and 14.2 g (0.18 mole) of pyridine were dissolved in 150 ml of methylene dichloride. To this solution, cooled in an ice-bath, three 6.6 g (0.08 mole) portions of methylsulfenyl chloride was added dropwise. The temperature was maintained at about 0° C throughout each addition and the resulting mixtures were stirred for about ½ hour at about 30° C after the completion of each addition.

The reaction mixture was then diluted with 150 ml of methylene dichloride, washed with water and evaporated under reduced pressure to remove the methylene dichloride. The residue was chromatographed in silica gel using hexane/ether. The yield of product was 14.4 g. The infrared and NMR spectra were consistent with the assigned structure. The elemental analysis om the product is tabulated in Table I.

EXAMPLE 4

Preparation of
2,3-dihydro-2,2-dimethyl-7-benzofuranyl N-methyl N-p-chlorophenylthiocarbamate In a 100 ml flask, 5.00 g (0.0226 mole) of 2,3-dihydro-2,2-dimethyl-7-benzofuranyl N-methyl carbamate and 1.97 g (0.025 mole) of pyridine were dissolved in 30 ml of dimethylformamide. To this solution, 4.48 g (0.025 mole) of p-chlorophenylsulfenyl chloride was added dropwise. The temperature was maintained at 30° C throughout this addition. The resulting mixture was stirred for 2½ hours at 30° C.

At the end of this time, 100 ml of benzene and 500 ml of water were added. The two resulting layers were separated, and the aqueous layer was extracted with 100 ml of benzene. This extract was added to the organic layer, and the combined material was washed first with 10% sodium bicarbonate and then with water. After drying and decolorizing, the solvent was removed by evaporation to leave 4.6 g of crude product. The infrared spectra showed strong adsorption peaks at 5.7, 6.75, 7.6–7.7, 7.9–8.1, 8.8–9.0, 9.9, 11.4, 12.3 and 13.1–13.4 microns. Elemental analysis on the product is tabulated in Table I.

EXAMPLE 5

Preparation of N-methyl-N-trichlorovinylthio-2,3-dihydro-2,2-dimethyl-7-benzofuranyl carbamate A 3.4 g (0.008 mole) sample of N-methyl-N-1,1,2,2-tetrachloroethylthio2,3-dihydro-2,2-dimethyl-7-benzofuranyl carbamate was dissolved in 100 ml dimethyl ether and cooled to 0° C in an ice bath. A 0.85 g (0.0085 mole) sample of triethylamine in 20 ml dimethyl ether was added dropwise and the resulting solution was stirred for 2 days at about 25° C. Analysis of the solution showed that no dehydrochlorination occurred. A 0.41 g (0.0085 mole) of sodium hydride (50% dispersion in mineral oil) was then added. The reaction mixture was heated at reflux for about 17 hours and then evaporated. Benzene (100 ml) was added and the reaction mixture was refluxed for about 24 hours. The reaction mixture was evaporated under reduced pressure and chromatographed on silica gel using hexane/benzene eluants to give 1.7 g of the product as an oil. Elemental analysis on the product is tabulated in Table I.

EXAMPLE 6

Preparation of 2,3-dihydro-2,2-dimethyl-7-benzofuranyl Chloroformate

A 7.9 g. (0.1 mol) sample of pyridine was added dropwise to a solution of 16.4 g. (0.1 mol) 2,3-dihydro-2,2-dimethyl-7-benzofuranol and 9.9 g. (0.1 mol) phosgene in 100 ml. benzene at about 25° C. The reaction mixture was stirred at 25° C for 2 hours, filtered and evaporated under reduced pressure. The solid residue was washed with hexane and dried to give the product, m.p. 85°–87.5° C. Elemental analysis for $C_{11}H_{11}O_3Cl$ showed:

|  | Calculated | Found |
|---|---|---|
| % Cl | 15.6 | 14.6 |

The chloroformate product can be reacted with sulfenylated amines, such as N-trichloromethylthio-N-methylamine (Example 1) or N-1,1,2,2-tetrachloroethylthio-N-methylamine, in the presence of pyridine to produce the compounds of the invention according to equation 4.

EXAMPLE 7

Preparation of bis-[O-(2,31-dihydro-2,2-dimethyl-7-benzofuranyl)-N-methylcarbamyl] sulfide A 9.37 g. (0.09 mol) sample of sulfur dichloride was added dropwise to solution of 33.15 g. (0.15 mol) 2,3-dihydro-2,2-dimethyl-7-benzofuranyl carbamate, 18.96 g. (0.24 mol) pyridine and 100 ml. methylene dichloride while heating under reflux. After the completion of the addition, the reaction mixture was heated under reflux an additional ½ hour. The reaction mixture was cooled, washed with water, 5% aqueous sodium bicarbonate solution, dried over magnesium sulfate and evaporated under reduced pressure to give 26.3 g. of the crude product. Recrystallization from isopropyl alcohol gave product melting at 131°–132° C. Elemental analysis showed:

|  | Calculated | Found |
|---|---|---|
| % S | 6.78 | 6.52 |

The bis[O-(2,3-dihydro-2,2-dimethyl-7-benzofuranyl]-N-methyl carbamyl] sulfide product gave 100% control of aphids at a concentration of 0.64 ppm and 100% control of American cockroaches at a concentration of 100 ppm by procedures identical to those employed for the compounds tabulated in Table II, page 18 of the specification.

Bis[O-(2,3-dihydro-2,2-dimethyl-7-benzofuranyl]-N-methyl carbamyl] sulfide is exemplary of compounds of the formula VIII

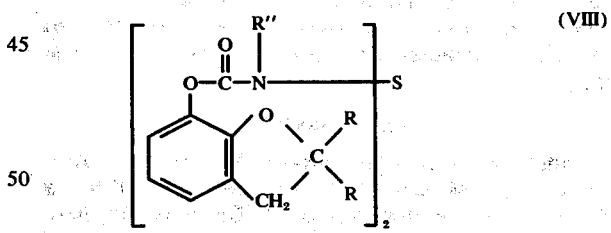

(VIII)

wherein R and R" have the same significance as defined in formula I. It is appreciated, of course, that the compounds of formula VIII correspond to those of formula (I) when R' is

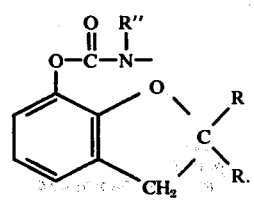

TABLE I

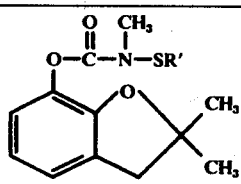

| No. | R' Substituent | M.P., °C. | Calculated S | C | H | N | Cl | Br | Found S | C | H | N | Cl | Br |
|---|---|---|---|---|---|---|---|---|---|---|---|---|---|---|
| 1 | trichloromethyl | 87–88 | | 42.1 | 3.8 | 3.8 | | | | 44.0 | 3.8 | 3.6 | | |
| 2 | 1,1,2,2-tetra-chloroethyl | 84–84.5 | | 40.1 | 3.6 | 3.3 | | | | 41.5 | 3.8 | 3.4 | | |
| 3 | methyl | Oil | 12.0 | | | | | | 11.3 | | | | | |
| 4 | 4-chlorophenyl | | 8.8 | | | | 9.8 | | 8.9 | | | | 10.2 | |
| 5 | trichlorovinyl | Oil | | 43.9 | 3.7 | 3.7 | | | | 44.2 | 3.6 | 3.6 | | |
| 6 | butyl | Oil | 10.4 | | | | | | 10.9 | | | | | |
| 7 | ethyl | Oil | 11.4 | | | | | | 11.5 | | | | | |
| 8 | dodecyl | Oil | 7.6 | | | | | | 7.4 | | | | | |
| 9 | phenyl | Oil | 9.7 | | | | | | 10.1 | | | | | |
| 10 | 4-methylphenyl | Oil | 9.3 | | | | | | 10.8 | | | | | |
| 11 | 3,4-dichlorophenyl | 78–81 | 8.1 | | | | 17.8 | | 8.1 | | | | 17.6 | |
| 12 | 2,5-dichlorophenyl | 102  103 | 8.1 | | | | 17.8 | | 8.2 | | | | 17.9 | |
| 13 | 4-bromophenyl | Oil | 7.9 | | | | | 19.6 | 7.9 | | | | | 19.6 |
| 14 | 4-fluorophenyl | Oil | 9.2 | | | | | 5.5* | 9.6 | | | | | 5.6* |
| 15 | 4-nitrophenyl | Oil | 9.6 | | | | | | 9.2 | | | | | |
| 16 | 4-t-butylphenyl | 119–122 | 8.4 | | | | | | 8.4 | | | | | |
| 17 | pentachlorophenyl | 152–154 | 6.4 | | | | 35.3 | | 6.7 | | | | 35.4 | |

*F in place of Br.

UTILITY

The benzofuranyl carbamates of this invention are used to control insects and are especially effective against cockroaches, aphids, flour beetles and mosquitos. In many instances the benzofuranyl carbamates of this invention exhibit significantly better insecticidal activity than the nonsulfenated benzofuranyl carbamates from which the benzofuranyl carbamates of this invention may be derived.

Representative benzofuranyl carbamates of this invention were tested as follows to illustrate the insecticidal and toxicity properties of this grouping. For comparison purposes, the insecticidal activity and toxicity of N-methyl 2,3-dihydro-2,2-dimethyl-7-benzofuranyl carbamate (marketed by Niagara Chemical Division of FMC Corporation as FURADAN) were also tested by the same procedures. Test results are provided in Table II.

Test Procedures

Aphids (*Aphis gossypii* Glover): An acetone solution containing 0.64 ppm of the candidate toxicant and a small amount of nonionic emulsifier was prepared. Cucumber leaves infested with the aphids were dipped into the toxicant solution. Mortality readings were then taken after 24 hours.

American Cockroach (*Periplaneta americana* L.): A 100 ppm acetone solution of the candidate toxicant was placed in a microsprayer (atomizer). A random mixture of anesthetized male and female cockroaches was placed in a container and 55 mg of the above-described acetone solution was sprayed on them. A lid was placed on the container. A mortality reading was made after 24 hours.

The test was also repeated with a 16 ppm acetone solution of the candidate toxicant.

Flour Beetle (*Tribolium confusum* DuVal): A 25 g sample of wheat grain was placed in a container and evenly coated with 0.5 ml of an acetone/water solution (acetone/water volume ratio of 1:19) containing 5 ppm of the candidate toxicant. The treated grain was then infested with 10 beetles. Mortality counts were made after one week exposure to the treated wheat.

Mosquito larvae (*Aedes aegypti*): 100 ml of water containing 0.5 ppm of the candidate toxicant and 10 fourth stage mosquito larvae were placed in a container. The container was placed in a controlled environment at 80° F. Mortality readings were taken after 48 hours.

Acute Oral Toxicity: The $LD_{50}$ of the candidate compound was determined by oral administration of the candidate toxicant in corn oil to rats having average weights of 125–175 g.

TABLE II

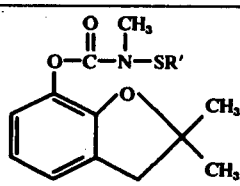

| Compound No. | R' Substituent | Aphids 4 ppm | 0.64 ppm | Cockroach 100 ppm | 16 ppm | Flour Beetle 5 ppm | Mosquito 0.05 ppm | Oral Toxicity Rats LD 50 |
|---|---|---|---|---|---|---|---|---|
| 1 | trichloromethyl | 100 | 91 | 100 | 15 | 100 | 46 | 125–250 |
| 2 | 1,1,2,2-tetrachloro- | | | | | | | |

TABLE II-continued

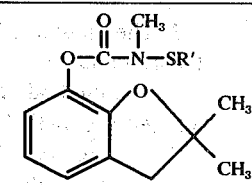

| Compound No. | R' Substituent | Aphids 4 ppm | Aphids 0.64 ppm | Cockroach 100 ppm | Cockroach 16 ppm | Flour Beetle 5 ppm | Mosquito 0.05 ppm | Oral Toxicity Rats LD 50 |
|---|---|---|---|---|---|---|---|---|
|  | ethyl | 98 | 97 | 67 | 7 | 100 | — | >125 |
| 3 | methyl | 100 | 97 | 100 | 100 | — | — | 5–25 |
| 4 | p-chlorophenyl | 100 | 97 | 100 | 5 | 96 | 100 | 25–41 |
| 5 | trichlorovinyl | 100 | 100 | 100 | 47 | — | — | — |
| 6 | butyl* | 100 | 97 | 100 | 95 | — | 100 | 60–125 |
| 7 | ethyl* | — | 92 | — | — | — | 26 | 25–125 |
| 8 | dodecyl | 100* | — | 20 | 0 | — | — | >125 |
| 9 | phenyl | 100 | 98 | 100 | 37 | — | — | 25–125 |
| 10 | 4-methylphenyl | 100 | 96 | 100 | 2 | 76 | — | 25–125 |
| 11 | 3,4-dichlorophenyl | — | 97 | — | — | — | 100 | 25–125 |
| 12 | 2,5-dichlorophenyl | — | 61 | — | — | — | 100 | 25–125 |
| 13 | 4-bromophenyl | — | 98 | — | — | — | 93 | 25–125 |
| 14 | 4-fluorophenyl | — | 92 | — | — | — | 100 | 25–125 |
| 15 | 4-nitrophenyl | 100 | 96 | 100 | 97 | — | — | 25–60 |
| 16 | 4-t-butylphenyl | 100* | — | 67 | 0 | — | — | 125–250 |
| 17 | pentachlorophenyl | 50* | — | 90 | 0 | — | — | 25–125 |
|  | FURADAN | 100 | 73–98 | 100 | 100 | 10 | 0 | 11 |

*40 ppm

The benzofuranyl thiocarbamates of this invention are also effective for the control of houseflies (*Musca domestica L.*), Milkweed bugs (*Oncopeltus fasciatus Dallas*) and cabbage looper (*Trichoplusia ni Hubner*).

The compounds of this invention are toxic to a variety of crop and household pests, in addition to the typical pests exemplified above. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5–80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from 1 percent to 15 percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For application these concentrates are dispersed in water or other liquid carrier, and normally applied as a spray to the area to be treated.

Other useful formulations for insecticical applications include simple solutions of the active ingredient in a dispersant in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprises 0.5 to 95% of the toxicant by weight of the pesticidal composition.

The pesticidal compositions may be formulated and applied with other active ingredients, including other nematocides, insecticides, fungicides, bactericides, plant growth regulators, fertilizers, etc. In applying the chemical an effective amount and concentration of the toxicants of this invention is, of course, employed.

The term "insecticide" and "insect" as used herein refer to their broad and commonly understood usage rather than to those creatures which in the strict biological sense are classified as insects. Thus, the term "insect" is used not only to include small invertebrate animals belonging to the class *Insecta*, but also to other related classes of arthropods whose members are segmented invertebrates having more or fewer than six legs, such as spiders, mites, ticks, centipedes, worms and the like.

As will be evident to those skilled in the art, various modifications on this invention can be made or followed, in the light of the foregoing disclosure and discussion, without departing from the spirit or scope of the disclosure or from the scope of the following claims.

I claim:

1. A method for killing insects which comprises contacting said insects or their hosts with an insecticidally effective amount of a compound of the formula

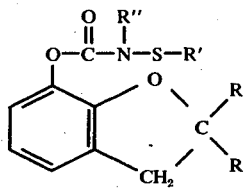

wherein
R and R'' individually are hydrogen or alkyl of 1 to 4 carbon atoms;
R' is alkyl of 1 to 12 carbon atoms; alkenyl of 2 to 12 carbon atoms; monocyclic or bicyclic aryl of 6 to 10 carbon atoms; alkyl of 2 to 12 carbon atoms substituted with 1 to 5 fluorine, chlorine or bromine atoms; alkenyl of 2 to 12 carbon atoms substituted with 1 to 5 fluorine, chlorine or bromine atoms; monocyclic or bicyclic aryl of 6 to 10 carbon atoms substituted with 1 to 5 fluorine, chlorine or bromine atoms, or 1 to 2 nitro groups; or

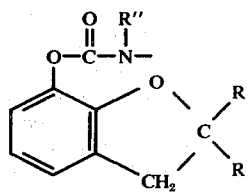

wherein R and R'' individually are hydrogen or alkyl of 1 to 4 carbon atoms.

2. The method of claim 1 wherein R and R'' are methyl.
3. The method of claim 1 wherein R' is alkyl of 2 to 6 carbon atoms.
4. The method of claim 3 wherein R' is ethyl and R and R'' are methyl.
5. The method of claim 3 wherein R' is butyl, and R and R'' are methyl.
6. The method of claim 1 wherein R' is alkyl of 2 to 3 carbon atoms substituted with 1 to 5 fluorine, chlorine or bromine atoms.
7. The method of claim 6 wherein R' is 1,1,2,2-tetrachloroethyl, and R and R'' are methyl.
8. The method of claim 1 wherein R' is monocyclic or bicyclic aryl of 6 to 10 carbon atoms.
9. The method of claim 1 wherein R' is phenyl substituted with 1 to 5 halogens.
10. The method of claim 9 wherein the halogen is chlorine or fluorine.
11. The method of claim 10 wherein R' is p-chlorophenyl, and R and R'' are methyl.
12. The method of claim 11 wherein R' is p-bromophenyl, and R and R'' are methyl.
13. The method of claim 1 wherein R' is phenyl substituted with 1 to 2 nitro groups.
14. The method of claim 1 wherein R' is

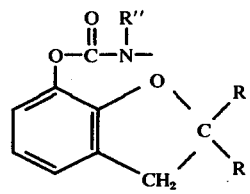

15. The method of claim 14 wherein R and R'' are methyl.
16. An insecticidal composition which comprises a biologically inert carrier and an insecticidally effective amount of a compound of the formula

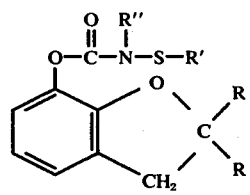

wherein
R and R'' individually are hydrogen or alkyl of 1 to 4 carbon atoms;
R' is alkyl of 1 to 12 carbon atoms, alkenyl of 2 to 12 carbon atoms; monocyclic or bicyclic aryl of 6 to 10 carbn atoms; alkyl of 2 to 12 carbon atoms substituted with 1 to 5 fluorine, chlorine or bromine atoms; alkenyl of 2 to 12 carbon atoms substituted with 1 to 5 fluorine, chlorine or bromine atoms; monocyclic or bicyclic aryl of 6 to 10 carbon atoms substituted with 1 to 5 fluorine, chlorine or bromine atoms, or 1 to 2 nitro groups; or

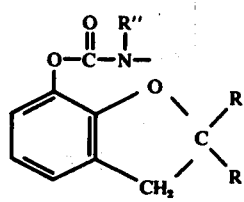

wherein R and R'' individually are hydrogen or alkyl of 1 to 4 carbon atoms.

17. The composition of claim 16 wherein R and R'' are methyl.

18. The composition of claim 16 wherein R' is alkyl of 2 to 6 carbon atoms.

19. The composition of claim 18 wherein R' is ethyl and R and R'' are methyl.

20. The composition of claim 18 wherein R' is butyl and R and R'' are methyl.

21. The composition of claim 16 wherein R' is alkyl of 2 to 3 carbon atoms substituted with 1 to 5 fluorine, chlorine or bromine atoms.

22. The composition of claim 21 wherein R ' is 1,1,2,2-tetrachloroethyl and R and R'' are methyl.

23. The composition of claim 16 wherein R' is monocyclic or bicyclic aryl of 6 to 10 carbon atoms.

24. The composition of claim 16 wherein R' is phenyl substituted with 1 to 5 halogens.

25. The composition of claim 24 wherein the halogen is chlorine or fluorine.

26. The composition of claim 25 wherein R' is p-chlorophenyl and R and R'' are methyl.

27. The composition of claim 26 wherein R' is p-bromophenyl and R and R'' are methyl.

28. The composition of claim 16 wherein R' is phenyl substituted with 1 to 2 nitro groups.

29. The composition of claim 16 wherein R' is

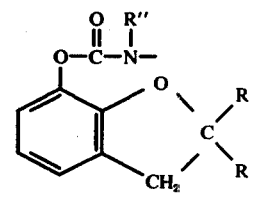

30. The composition of claim 29 wherein R and R'' are methyl.

* * * * *